Figure 1:
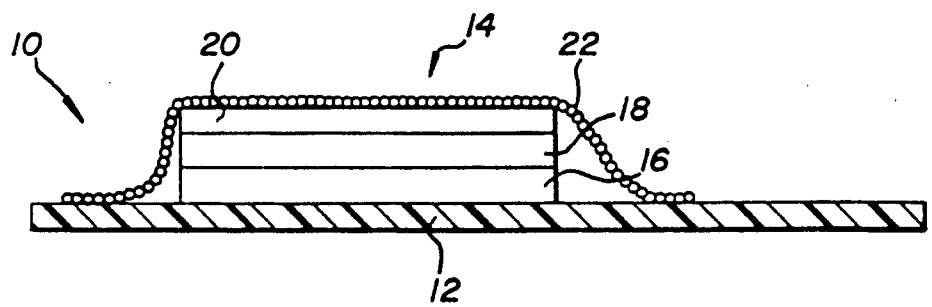

United States Patent [19]

Freitag et al.

[11] Patent Number: 5,037,736

[45] Date of Patent: Aug. 6, 1991

[54] PROCESS AND TEST CARRIER FOR THE DETERMINATION OF AN ANALYTE

[75] Inventors: Helmut Freitag, Indianapolis, Ind.; Hans-Erich Wilk, Lorsch; Anselm Rothe, Birkenau, both of Fed. Rep. of Germany

[73] Assignee: Boehringer Mannheim GmbH, Mannheim, Fed. Rep. of Germany

[21] Appl. No.: 122,185

[22] Filed: Nov. 18, 1987

[30] Foreign Application Priority Data

Nov. 26, 1986 [DE] Fed. Rep. of Germany ....... 3640318

[51] Int. Cl.$^5$ .................. G01N 33/53; G01N 33/543; G01N 33/536; C12Q 1/34
[52] U.S. Cl. ........................................ 435/7.9; 422/56; 435/7.1; 435/7.92; 435/7.95; 435/10; 435/18; 435/174; 436/501; 436/518; 436/528; 436/529; 436/536; 436/537; 436/540; 436/547; 436/823
[58] Field of Search ........................ 435/7, 18, 10, 7.1, 435/7.9, 7.92, 7.95, 174; 436/501, 518, 528, 529, 537, 540, 547, 548, 820, 823, 536; 422/56

[56] References Cited

U.S. PATENT DOCUMENTS

| 3,964,871 | 6/1976 | Hochstrasser | 435/10 |
|---|---|---|---|
| 4,510,239 | 4/1985 | Miller et al. | 436/540 |
| 4,513,088 | 4/1985 | Levy et al. | 436/518 |
| 4,629,697 | 12/1986 | Limbach et al. | 435/10 |
| 4,661,445 | 4/1987 | Saxinger et al. | 436/518 |
| 4,743,544 | 5/1988 | Namba et al. | 436/518 |
| 4,804,625 | 2/1989 | Morrison et al. | 436/518 |
| 4,806,312 | 2/1989 | Greequist | 422/56 |
| 4,868,131 | 9/1989 | Hiratsuka | 422/56 |

FOREIGN PATENT DOCUMENTS 0139389  5/1985  European Pat. Off. ............ 436/540

OTHER PUBLICATIONS

Oellerich, J. Clin. Chem. Biochem., vol. 22, 1984, pp. 895-904.

Primary Examiner—Esther L. Kepplinger
Assistant Examiner—Florina B. Hoffer
Attorney, Agent, or Firm—Armstrong, Nikaido, Marmelstein, Kubovcik & Murray

[57] ABSTRACT

The present invention provides a process for the determination of an analyte in a body fluid, in which there are used two binding components capable of specifically binding with one another, one of the binding components being enzyme-labelled and not carrier-fixed and the other binding component being carrier-fixed. The process contains a step in which the binding components are incubated with one another so that binding reaction takes place. The amount of enzyme-labelled binding component not bound to the carrier-fixed binding component is a measure of the concentration of the analyte which is determined by allowing the labelling enzyme to act upon a substrate producing a detection signal. During the specific binding reaction, incubation is carried out simultaneously with a non-fixed substrate of the labelling enzyume which does not produce a detection signal and with a carrier-fixed substrate of the labelling enzyme which produces a detection signal, the substrate not producing a detection signal being so chosen with regard to the amount used and affinity to the labelling enzyme in relation to the amount of the substrate producing a detection signal and its affinity to the labelling enzyme and in relation to the total activity of the labelling enzyme that the enzyme-catalyzed reaction of the substrate producing a detection signal is delayed until the specific binding reaction between the binding components has substantially taken place.

19 Claims, 1 Drawing Sheet

PROCESS AND TEST CARRIER FOR THE DETERMINATION OF AN ANALYTE

The present invention is concerned with a process for determining an analyte in a sample, especially in a body fluid, with the help of biomaterials which are specifically capable of binding with one another, as well as with a test carrier for carrying out the process.

In particular, the present invention is concerned with immunological detection processes. For many years, these have played a considerable part in analytical investigations, especially in the quantitative and qualitative determination of components of body fluids, such as blood or urine. They are characterised in that they are highly specific and extremely sensitive. The detection processes are based on the immunological interaction between the analyte and a biomaterial binding with this analyte with high specificity. The analyte can thereby be either the sought after component of the body fluid itself or a substance derived therefrom in a preceding step, the amount of which is characteristic for the amount of the sought after component in the sample.

By the labelling of one of the binding components of the immunological determination, there can be determined the degree of the reaction and thus the concentration of the analyte to be measured. Various immunological determination processes are differentiated according to the selected labelling. The present invention is only directed towards the so-called enzyme immunoassays where an enzyme is used for labelling. The detection of the enzyme is done such as it is also usual in the case of enzyme diagnosis in which the enzyme is allowed to act upon a substrate.

The substrate is thereby so chosen that its change catalysed by the enzyme gives rise to a detectable signal. In the simplest case, the change results in a change of the colour of the substrate which is either directly visibly recognisable or, for a quantitative evaluation, can be measured with the help of an appropriate photometer. However, the expression "a substrate producing a detection signal" is to be broadly understood to cover every case in which there arises any recognisable or measurable signal as the result or also possibly the indirect result of the action of the labelling enzyme on the substrate. For example, it covers cases in which the substrate itself admittedly shows no colour change but initiates a subsequent reaction leading to a colour change. It also includes cases in which a signal other than a colour change is measured, for example luminescence.

Apart from immunological processes, the present invention is also directed towards other analytical processes in which, in the course of a quantitative or qualitative determination of an analyte, two substances specifically capable of binding with one another, which are generally referred to as binding components, are used. The binding components are mostly not only capable of binding with one another but at least one of the binding components makes a specific binding reaction with the analyte or an analyte-specific product of a preceding reaction.

In the case of an especially important group of such processes, one of the binding components, for example an antibody, is enzyme-labelled and not carrier fixed, i.e. is freely mobile in the test. The other binding component, for example an antigen, is carrier fixed. The total reaction of the analytical determination contains, possibly after one or more preceding steps, a reaction step in which the binding components are incubated with one another so that a specific binding reaction takes place between them, whereby, after completion of the specific binding reaction, the amount of the enzyme-labelled binding component not bound to the carrier-fixed binding component is a measure for the concentration of the analyte. This amount is determined with the help of the enzyme labelling by allowing the labelling enzyme to act upon a substrate producing a detection signal. In the following, there are described some important examples of such processes.

In the case of a first variant, the carrier-fixed binding component is a biomaterial which is capable of binding specifically not only with the enzyme-labelled, non-carrier-fixed binding component but also with the analyte. The enzyme-labelled binding component is thus an analogue of the analyte. Both are simultaneously incubated with the carrier-fixed binding component, this being present in excess with regard to the enzyme-labelled non-fixed binding component. The analyte and the enzyme-labelled analyte analogue compete for the limited number of binding places on the carrier-fixed binding component. Therefore, these are also called competitive tests.

If, for example, it is desired to determine an antigen, then this is simultaneously incubated with a definite amount of enzyme-labelled antigen and of an amount of a carrier-fixed antibody present in excess in comparison therewith until the immunological binding reaction has taken place. The antigen from the sample and the enzyme-labelled antigen from the reagent thereby compete for the binding places on the carrier-fixed antibody. The more non-labelled antigen is present in the sample, then the less enzyme-labelled antigen is bound to the carrier-fixed antibody. The amount of the remaining non-bound, enzyme-labelled antigen is thus then a measure of the amount of antigen in the sample.

In the case of another variant of such a process, the non-carrier-fixed, enzyme-labelled binding component is specifically capable of binding not only with the carrier-fixed binding component but also with the analyte. For example, a non-fixed, enzyme-labelled antibody can be used which is specific not only for a carrier-fixed antigen present in the test but also for antigen from the sample. In the case of such a test composition, it is then possible so to proceed, on the one hand, that first in a pre-reaction, which precedes the reaction step in which the enzyme-labelled, non-carrier-fixed binding component and the carrier-fixed binding component are incubated with one another, the enzyme-labelled, non-carrier-fixed binding component is incubated with the analyte. Thus, in this example, the enzyme-labelled antibody is first allowed to react with the sample antigen. In the case of the known processes, the antibody is thereby present in excess of the maximum possible amount of antigen in the sample so that an amount of an antigen-antibody complex is formed corresponding to the amount of the sample antigen. Only after the completion of this pre-reaction is the result of the reaction brought into contact with the solid phase-bound antigen which is usually present in excess with regard to the enzyme-labelled antibody. In this reaction step between the two biomaterials in the test which are specifically bindable with one another, i.e. enzyme-labelled free antibody and carrier-fixed antigen, the part of the enzyme-labelled antibody not complexed in the preceding reaction step is bound by the carrier-fixed antigen and thus is no longer freely mobile. In the case of this carrying out of the test, the amount of the finally still freely mobile enzyme-labelled binding component, i.e. not bound to the carrier-fixed binding component, thus corresponds to the amount of the analyte in the sample. This test principle is known as the IEMA test.

Alternatively, instead of the two-step process method, here too it is possible to proceed in one step, i.e. analyte, enzyme-labelled, non-carrier-fixed binding component (enzyme-labelled-antibody) and carrier-fixed binding component (carrier-fixed antigen) are incubated simultaneously. In this case, the binding reactions between the enzyme-labelled binding component and the analyte take place on the one hand, as well as between the enzyme-labelled binding component and the carrier-fixed binding component on the other hand in competition to one another. Here, too, the result is that the amount of the freely mobile enzyme-labelled binding component remaining in the test is a measure for the concentration of the analyte.

Over and above the previously mentioned examples, the present invention is also directed to any analytical determination process in which two binding components specifically bindable with one another present in the test composition are so incubated with one another that, after completion of the specific binding reaction, the amount of the enzyme labelling present in the free phase is determined as a measure of the concentration (or in the case of qualitative tests, as measure for the presence) of an analyte.

Since, in the case of these analytical determination processes, the enzyme activity in the free phase must be measured separately from the simultaneously present bound (carrier-fixed) phase, in the usual processes, spatial separation of the bound and of the free phases is necessary. In the practical carrying out of the determinations, this involves a considerable expense. Since the exactitude of the analysis is directly influenced by the quality with which the bound and the free phases are separated from one another, a plurality of washing steps is regularly carried out. Insofar as the determinations are carried out manually with the help of appropriate reagents, this is very time-consuming. Apparatus have already been developed for the mechanical carrying out of such determinations. However, because of the complexity of the procedures, these are laboriously constructed and thus expensive and their handling requires trained personnel.

In contradistinction thereto, there has long been a need for appropriate methods of determination which are simple to handle. This would be desirable, especially in the case of the transmission of the known immunological methods to carrier-bound tests. Such test carriers, which are also referred to as so-called dry tests, have long been known for non-immunological determinations. They have, for example, the form of known test strips in which the actual reaction region is present in the form of a test field. Another embodiment is made as a substantially quadratic platelet. Here, the reaction region is also present in quadratic form in the middle of the platelet and, in the case of the most usual embodiments, is produced in the manner of a photographic film in a layered process.

A series of experiments have already been carried out to transfer determinations of the type in question, especially immunological determinations, to test carriers. Thus, for example, test strips are available which only carry a part of the mentioned test components. These must then be dipped successively and in a definite chronological rhythm into several liquids. The desired simple handling is thereby not achieved.

In Federal Republic of Germany Patent Specification No. 32 37 046, there is described a device and a process for the determination of the presence of antigens with the help of test carriers. The device has at least two zones, one of which can be called a substrate zone and the other an immunological reaction zone. By means of a particular choice of the components in the immunological reaction zone, it is now to be achieved that only those enzyme-labelled ligands reach the substrate zone which are characteristic for the presence or amount of the analyte although both zones are continuously in liquid contact with one another, as is usual in the case of the various layers of a multi-layer test carrier.

In practice, the test carriers described in Federal Republic of Germany Patent Specification No. 32 37 046 have not proved to be useful. This may be due to the fact that, inter alia, it is not possible to prevent a part of the excess of enzyme-labelled antibody unavoidably penetrating into the substrate zone and thereby falsifying the measurement result.

Therefore, it is an object of the present invention to improve determinations of the initially defined type in that they can be carried out without spatial separation between free and bound phases. There are thereby to be made available especially test carriers which are easy to handle and, nevertheless, provide dependable results.

Thus, according to the present invention, there is provided a process for the determination of an analyte in a sample, especially in a body fluid, in which there are used two biomaterials (binding components) capable of specifically binding with one another, one of the binding components being enzyme-labelled and not carrier fixed and the other binding component being carrier-fixed, which process contains a step in which the binding components are incubated with one another so that a specific binding reaction can take place between them, whereby, after ending of the specific binding reaction, the amount of enzyme-labelled binding component not bound to the carrier-fixed binding component is a measure for the concentration of the analyte and this amount is determined with the help of the enzyme labelling by allowing the labelling enzyme to act upon a substrate producing a detection signal, wherein, during the specific binding reaction, incubation is carried out simultaneously with a non-fixed substrate of the labelling enzyme which does not produce a detection signal and with a carrier-fixed substrate of the labelling enzyme which produces a detection signal, the substrate not producing a detection signal being so chosen with regard to the amount used and affinity to the labelling enzyme in relation to the amount of the substrate producing a detection signal and its affinity to the labelling enzyme and in relation to the total activity of the labelling enzyme that, in the case of simultaneous incubation of the enzyme-labelled, non-carrier-fixed binding component with both substrates, the enzyme-catalysed reaction of the substrate producing a detection signal is delayed until the specific binding reaction between the binding components has substantially taken place.

The present invention also provides a test carrier for the determination of an analyte in a sample, especially in a body fluid, with a reaction zone to which a sample can be applied, wherein the reaction zone contains the following reaction components in such an arrangement that, when using the test carrier, they are simultaneously incubated: two binding materials (binding components) capable of specific binding with one another, one of which binding components is enzyme-labelled and soluble and the other is carrier-fixed, a non-fixed substrate of the labelling enzyme which does not produce a detection signal and a carrier-fixed substrate of the labelling enzyme which produces a detection signal, the substrate not producing a detection signal being so chosen with regard to the amount used and the affinity to the labelling enzyme in relation to the amount of the substrate producing a detection signal and its affinity to the labelling enzyme and in relation to the total activity of the labelling enzyme that, in the case of simultaneous incubation of the first enzyme-labelled binding component with the two substrates, the enzyme-catalysed reaction of the substrate producing a detection signal is delayed until the specific binding reaction between the enzyme-labelled binding component and the carrier-fixed binding component is substantially ended.

An important feature of the present invention is that the detection reaction is chronologically delayed but not spatially separated. As mentioned above, the detection signal can be produced in different ways. In the following description, by way of example, the commonest case is used as a starting point, namely, the colour of the enzyme substrate changes due to the action of the enzyme. However, the generality of the possible detection reactions is thereby not to be limited in any way.

The chronological delay is achieved in that a non-fixed and thus, in the case of practical use, freely mobile substrate which does not produce a detection signal, is used simultaneously with a carrier-fixed and thus not freely mobile substrate of the labelling enzyme producing a detection signal, both substrates thereby being present already during the course of the specific, especially immunological binding reaction. It is not necessary that the substrates are incubated together with the ligands during the total course of the specific binding reaction. On the contrary, the process can also take place in such a manner of the test can be so constructed that a part of the binding reaction has already taken place before a contact with the substrates takes place. However, it is important that as soon as the substrate producing a detection signal comes into contact with the labelling enzyme, the substrate not producing a detection signal is simultaneously present. It is thereby achieved that it is not harmful when, at least during a part of the time in which the specific binding reaction takes place, this takes place with simultaneous contact with the substrate.

Consequently, the expression "substrate not producing a detection signal" is to be understood to mean that the substrate does not produce a signal disturbing the practical measurement in comparison with the substrate producing a detection signal. Thus, insofar as, as mentioned, a colour change is used, the colour change of the substrate not producing a detection signal, i.e. the non-colour-forming substrate, must, under the measurement conditions, be so much smaller than that of the substrate producing a detection signal, i.e. the colour-forming substrate, that the measurement result is not disturbed within the scope of the measurement exactitude aimed for. Thus, in the case of a visual evaluation, no disturbing colour change of the non-colour-forming substrate must be present in the whole of the range of visible light. In the case of an evaluation with the use of apparatus, it is sufficient when the substrate displays no disturbing colour change in the measurement wavelength of the appropriate evaluation apparatus.

In the following, the substrate producing a detection signal (carrier-fixed) is designated with S and the substrate not producing a detection signal (free) is designated with $S_0$. The presence of $S_0$ has the result that the detection signal of S first starts chronologically delayed, namely, when the simultaneously proceeding specific binding reaction between the enzyme-labelled free binding component and the solid phase-bound binding component has substantially taken place. This is achieved because the labelling enzyme first comes together, with a very much greater degree of probability, with the free substrate and catalyses its reaction than with the solid phase-bound substrate. However, the reaction of $S_0$ does not lead to a detection signal so that, in this phase, no signal is measured.

The rate with which an enzyme-catalysed reaction of a substrate takes place depends upon the total activity of the enzyme used, the affinity between substrate and enzyme and the amount of substrate. This applies not only to S but also to $S_0$. Furthermore, it is important for the present invention that, in the case of the simultaneous presence of two substrates of an enzyme, one of which is solid phase-bound and the other freely mobile, the enzyme-catalysed reaction of the bound substrate takes place only to a very greatly reduced extent until the free substrate has been substantially consumed.

The desired delay of the enzyme-catalysed reaction of S is, therefore, dependent upon the affinity and amount of $S_0$ used. These are to be fixed in relation to the total activity of the labelling enzyme in the test. The higher is the activity of the enzyme and the higher is its affinity to $S_0$, the more quickly is it consumed. Furthermore, the amount and the affinity of S plays a part in the delay, as is explained in more detail in the following. In total, on the basis of the teachings of the present invention, as well as by theoretical considerations and also by practical testing, it can be determined whether, with the particular $S_0$ used and with the amount thereof employed, a sufficient delay is achieved.

As mentioned, it is of importance that the amount of $S_0$ used, its affinity for the labelling enzyme and the total activity of the labelling enzyme in the test are correctly adapted to one another. The affinity depends upon the selected substrate and the labelling enzyme and can, therefore, only insofar be freely determined as appropriate substrates are available for the enzyme in question. The amount of substrate is also not freely selectable without limitation. Therefore, according to a preferred embodiment of the present invention, in cases in which the delay achieved by a particular $S_0$ is to be shortened, the labelling enzyme is additionally used in carrier-fixed form, the enzyme-catalysed reaction of $S_0$ thereby being accelerated. On the other hand, the enzyme-catalysed reaction of S is not influenced by the carrier-bound enzyme because this substrate is also carrier-bound.

In order, on the other hand, to increase the delay of the detection reaction, i.e. in order to achieve a slower consumption of $S_0$, according to another preferred embodiment of the present invention, it can be preferable to label enzymatically only a part of the free, first binding component. The total activity of the labelling enzyme in the test is thereby reduced and the enzyme-catalysed reaction of $S_0$ delayed.

By the combination of the above-mentioned measures, the period of delay after which the enzyme-catalysed reaction of S begins can be varied in wide ranges.

In this way, the particular velocity of the specific binding reaction between the first and second ligand can be well adapted. The mentioned delay is, in each case, so adjusted that the specific binding reaction has substantially taken place, the term "substantially" being understood with regard to the desired measurement exactitude. Insofar as the specific binding reaction has not completely taken place, the system of the participants of the specific binding reaction are not yet in equilibrium. Consequently, a part of the enzyme-labelled first binding component is still freely mobile which, in equilibrium, would be bound to the carrier-fixed second ligand. If, in this stage, the enzyme-catalysed reaction of S has already commenced, a measurement error results therefrom. The higher are the demands for measurement accuracy, the longer must the enzyme-catalysed reaction of S be delayed.

As mentioned hereinbefore, the period of delay with which the enzyme-catalysed reaction of S commences is also dependent upon the amount thereof and the affinity towards the enzyme. The enzyme preferably has a higher affinity towards the free $S_0$ than towards the bound S. It is thereby achieved that the reaction of S is only catalysed to a very small extent so long as a noteworthy amount of $S_0$ is still present.

Figure 2:
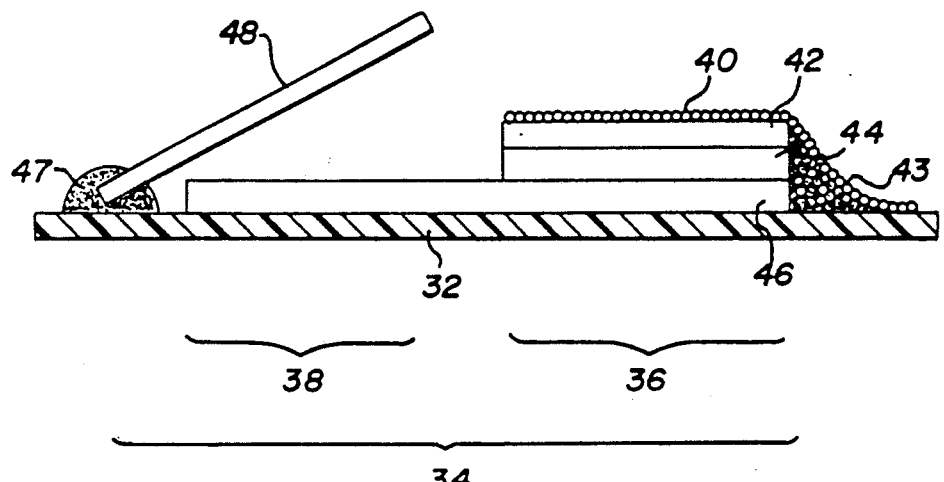
Figure 3:
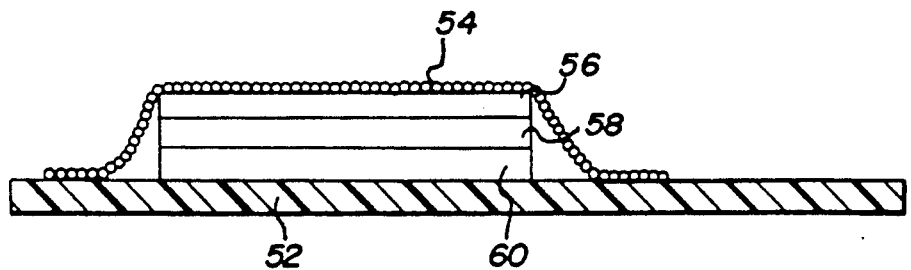

In the following, the present invention is explained in more detail on the basis of embodiments illustrated in the accompanying drawings, further preferred embodiments and the advantages achieved therewith also being explained. In the drawings, FIGS. 1, 2 and 3 show schematic cross-sections of various test carriers according to the present invention.

In FIG. 1, there can be seen a test carrier 10 which essentially consists of a longitudinally-extended base foil 12 and a reaction zone arranged thereon which, in total, is indicated by 14. The base foil 12 can, for example, be formed longitudinally, extending in the manner of a conventional test strip.

The reaction zone 14 has three different layers 16, 18 and 20 which are securely held on to the base foil 12 by a nylon mesh 22. The layers 16, 18 and 20 lie full-facedly on one another so that they are in contact with one another, making possible a liquid exchange. Each layer is formed, for example, as a quadratic platelet with the approximate dimensions of 6 mm.×6 mm. The layers are produced by processes conventionally used in the production of test strips and are attached to the base foil.

In order to be able to determine antigen contained in a liquid sample with the embodiment of the test carrier according to the present invention illustrated in FIG. 1, the upper layer 20 contains a conjugate of an antibody specific for the antigen and a labelling enzyme. The underlying layer 18 contains a non-colour-forming substrate $S_0$. The lowermost layer 16 contains a carrier-fixed, colour-forming substrate S for the labelling enzyme and a carrier-fixed antigen for which the antibody in the layer 18 is specific. Furthermore, the layer 16 contains carrier-fixed additional labelling enzyme if this is necessary according to above-described criteria.

When the test carrier illustrated in FIG. 1 is brought into contact with a sample, for example by briefly dipping in, the sample liquid dissolves the soluble antibody-enzyme conjugate in the layer 20 and the non-colour-forming substrate $S_0$ in the layer 18. Since the layers 16, 18 and 20 are in contact with one another, making possible a liquid exchange, the antibody-enzyme conjugate also penetrates into the layers 18 and 16 and the non-colour-forming substrate also into the layers 20 and 16. In all, there results a uniform, mutually incubated mixture in which all the described reaction components are simultaneously present so that not only the immunological binding reaction but also the enzyme-catalysed reactions of the substrates take place side by side.

The immunological test principle of the test illustrated in FIG. 1 follows the above-mentioned principle in which the antibody in the layer 20 binds specifically not only with the carrier-fixed antigen in the layer 16 but also with the antigen in the sample. Since the sample antigen and the antibody, after dissolving in the sample liquid, are freely mobile, a binding between these two components first takes place with a very much greater probability than the coupling of the antibody with the carrier-fixed antigen in the layer 16. When the antibody in the layer 20 is present in excess with regard to the sample antigen, the antigen contained in the sample is practically completely bound with the antibody. The complex formed is freely mobile in the reaction zone of the test carrier. Excess enzyme-labelled antibody binds to the carrier-fixed antigen in the layer 16 and is thereby fixed.

On the basis of its free mobility, the antigen-antibody complex comes into contact with the carrier-fixed substrate S in the layer 16 so that the labelling enzyme can catalyse the substrate reaction. The excess of the enzyme-labelled antibody bound to the carrier-fixed antigen and thus immobilised cannot, on the other hand, come into contact with the also carrier-fixed colour-forming substrate and, therefore, does not contribute to the colour formation. The colour formation is, therefore, a measure for the amount of antigen-antibody complex.

For the exactitude of the determination of the antigen, it is thereby important that the immunological binding reaction first takes place substantially so that the amount of antigen-antibody complex formed corresponds to the amount of the antigen in the sample, whereas, on the other hand, the excess of antibody is bound almost completely to the carrier-fixed antigen and thus removed from the reaction mixture. If the colour-forming reaction were to start before this state is reached, then enzyme-labelled antibody would still be present in the incubation mixture in freely mobile form which is not complexed with an antigen. If this were to come into contact with the carrier-fixed substrate and a colour formation were to be initiated, then the measurement result would be falsified. This is avoided by the delay with the help of the non-colour-forming substrate $S_0$.

On the basis of the previously described relationship according to the present invention between the substrates used and the labelling enzyme and on the basis of the fact that the colour-forming substrate is carrier-fixed, the enzyme reaction of $S_0$ is first preponderantly catalysed, which does not result in a colour formation. Only when $S_0$ has been substantially consumed does the labelling enzyme act to an increased extent also on the carrier-fixed substrate S which results in the colour formation.

The course of the colour formation for three different concentrations of non-colour-forming substrate $S_0$ is illustrated in the following Table 1. This Table is based on an example in which 0.1 mM chlorophenol red galactoside was used as colour-forming substrate S. It shows the colour formation without $S_0$ and with 1 mM, 5 mM and 10 mM nitrophenyl galactoside as $S_0$ ($\beta$- galactosidase 250 mU/ml.). It can clearly be seen that the colour formation commences with greater delay, the more non-colour-forming substrate is present.

TABLE 1

| time | [$S_0$] % colour formation | | | |
|---|---|---|---|---|
| | 0 mM | 1 mM | 5 mM | 10 mM |
| 2 minutes | 44 | 23 | 2 | 1 |
| 6 minutes | 99 | 98 | 9 | 4 |
| 10 minutes | 100 | 100 | 20 | 8 |
| 20 minutes | 100 | 100 | 96 | 20 |

The numerical values given in Table 1 only apply, of course, to a particular $S/S_0$ pair. However, the course of the colour-forming reaction is also similar for other compositions according to the present invention and, on the basis of the teachings of the present invention, can be varied to a comparatively wide extent by appropriate choice of the reaction components.

As mentioned, the labelling enzyme is incorporated in the layer 16 in carrier-fixed form. The enzyme activity in the test then consists of the sum of the labelling enzyme of the antibody from layer 18 and the fixed enzyme in layer 16. The reaction of the non-colour-forming substrate $S_0$ can be catalysed not only by the carrier-fixed enzyme but also by the labelling enzyme. $S_0$ is thereby more quickly consumed than if no carrier-fixed enzyme were used. Thus, the period of delay in the case of a given amount of $S_0$ is thereby shortened. The presence of the carrier-fixed enzyme has no influence on the reaction of the colour-forming substrate S because both reaction components are carrier-fixed and consequently cannot come into contact with one another.

The fact that the reaction components in the preferred embodiment of the present invention illustrated in FIG. 1 are arranged in three different layers of the test carrier, has preponderantly production-technical reasons. In the production of the carrier layers, the reaction components are usually impregnated on to a solid carrier matrix or are incorporated in an appropriate film from a liquid phase. Insofar as, in the case of this procedure, reaction components are simultaneously present which could react with one another, special measures must be resorted to in order to prevent such a reaction. Therefore, for the production, it is advantageous when, on the one hand, the antibody and the antigen and, on the other hand, the substrate and the labelling enzyme are incorporated into separate layers. In a concrete example, the antibody in layer 20 is separated from the antigen in layer 16. Furthermore, the enzyme labelling in the layer 20 is separated not only from the non-colour-forming substrate in the layer 18 but also from the colour-forming substrate in layer 16. Generally stated, it is advantageous when the first binding component which carries the enzyme labelling is contained in one layer which does not simultaneously contain one of the substrates and when the enzyme-labelled non-carrier-fixed binding component and the carrier-fixed binding component are contained in separate layers.

FIG. 2 shows an embodiment of the present invention such as is, in principle, known from the "Reflotron" analysis system of the present Applicants and from numerous publications, for example European Patent Specification No. 0,045,476.

A speciality of this system is the fact that the reaction zone 34, which in its totality is again carried by a base foil 32, can be divided up into an application zone 36 and into a detection zone 38.

The application zone 36 contains several layers arranged one on top of the other and, in the illustrated embodiment, under a covering mesh 40, a glass fibre layer 42, thereunder a reagent layer 44 which, again for the example of a determination of an antigen, contains an enzyme-labelled antibody in soluble form and thereunder a glass fibre fleece 46. The layers 42, 44 and 46 are fixed with a melt adhesive strip 43.

In the direction of the detection zone, the glass fibre fleece 46 has a greater dimensioning than the layers present thereover, i.e. it connects the application zone 36 with the detection zone 38. Over the part of the glass fibre fleece 46 not covered by the layers 42 and 44, there is present a flap 48 fixed with a melt adhesive strip 47 which is so produced that, without exerting an additional pressure, it is not in contact with the glass fibre fleece 46. However, manually or with the help of a mechanical part of the appropriate evaluation device, it can be pressed downwardly on to the glass fibre fleece 46 so that it comes into contact with this in a way making possible a liquid exchange.

The flap 48 contains a reagent film in which is present a soluble, non-colour-forming substrate $S_0$, as well as antigen in carrier-fixed form for which the antibody in the layer 44 is specific and a colour-forming substrate S for the labelling enzyme of the antibody in the layer 44, as well as optionally additional carrier-fixed labelling enzyme.

The test now takes place in such a manner that a sample, preferably blood, is applied in the form of a droplet to the application zone 36. It penetrates through the covering mesh 40 into the glass fibre layer 42 which serves to separate off the erythrocytes in the blood so that only plasma trickles through the glass fibre layer 42 and passes into the layer 44, as is described in more detail in the above-mentioned European Patent Specification No. 0,045,476.

The sample which penetrates into the layer 44 there dissolves the enzyme-labelled antibody. The antigen from the sample is bound by the enzyme-labelled antibody and an antigen-antibody complex results which is enzyme-labelled. Furthermore, after ending of this specific binding reaction between the sample antigen (analyte) and the enzyme-labelled antibody (non-carrier-fixed binding component), there is also present enzyme-labelled antibody in the layer 44 which is not bound with antigen.

The liquid with the mentioned reaction components passes further into the glass fibre fleece 46 and is transported by this, because of the capillary action, under the flap 48.

A substantial difference with regard to the embodiment illustrated in FIG. 1 is that in the case of the embodiment illustrated in FIG. 2, the point of time of the contact between the flap and the glass fibre fleece can be freely controlled. In other words, a first incubation phase, in which the specific binding reaction takes place between the analyte and the non-carrier-fixed binding component, can take place completely independently of a second incubation phase in which there are added the components contained in the flap. It is thereby possible to await the adjustment of the equilibrium between the analyte and the free binding component before the further reaction is initiated by pressing down the flap 48.

The specific binding reaction between the free, enzyme-labelled and the carrier-fixed binding components first begins when, after termination of the pre-reaction, the flap 48 is pressed down and thereby brought into contact with the glass fibre fleece 46. There now takes place the specific binding reaction between the enzyme-labelled antibody (free binding component) from the layer 44, insofar as it is not complexed with sample antigen, and carrier-fixed antigen (carrier-fixed binding component) on the flap 48. At the same time, the labelling enzyme catalyses, initially by far preponderantly, the reaction of the freely mobile non-colour-forming substrate $S_0$ dissolved by the sample liquid so that the colour-forming reaction of the carrier-fixed substrate S first occurs later at a point of time at which the specific binding reaction between the enzyme-labelled antibodies and the carrier-fixed antigen has substantially taken place. Therefore, in this example, too, in spite of simultaneous incubation of both reaction components and of the colour-forming substrate, the colour formation first commences at a point of time at which only so little non-complexed, enzyme-labelled antibody is present in the incubation mixture that it can practically no longer falsify the measurement result. The colour reaction practically detects only the still freely mobile enzyme-labelled complex of antigen and antibody.

In the case of the carrying out of the test explained on the basis of FIGS. 1 and 2, the free binding component is usually present in excess in comparison with the analyte and the carrier-fixed binding component in excess to the free binding component. However, this requires comparatively large amounts of the test components in question. The present invention is combined especially preferably with the invention described in Federal Republic of Germany Patent Specification No. 36 24 464, in which smaller amounts of the binding components can also be used.

The embodiment illustrated in FIG. 3 resembles in its construction that of FIG. 1. However, it differs in the coating of the various layers. In the case of this embodiment, too, a total of three layers are held in contact, making possible a liquid exchange, by a nylon mesh 54 on a base foil 52.

The uppermost layer 56 contains, again for the determination of an antigen as analyte of the sample, a conjugate of an antigen and a labelling enzyme. The middle layer 58 contains an antibody which specifically binds not only the antigen from the sample but also the antigen in the layer 56, in carrier-fixed form. Furthermore, it can contain labelling enzyme in carrier-fixed form.

Finally, the lowermost layer 60 contains the carrier-fixed, colour-forming substrate and the free, non-colour-forming substrate.

The test illustrated in FIG. 3 is of the competitive type, i.e. the carrier-fixed antibody (carrier-fixed binding component) binds specifically not only the antigen (analyte) from the sample but also the enzyme-labelled, free antigen (free binding component).

The sample antigen and the enzyme-labelled antigen from the layer 56 compete for the binding points on the carrier-fixed antibody in the layer 58. After ending of this competing specific binding reaction, the amount of non-bound, enzyme-labelled antigen is a measure for the sample antigen, whereby the more enzyme-labelled antigen remains free, the more antigen was present in the sample. Here, too, it is again necessary that the colour formation first commences when the described immunological binding reaction has almost completely finished. Were it to commence too early, then the measurement result would be falsified because the amount of the free enzyme-labelled antigen would still not be a reproducible measure for the amount of sample antigens. In this case, too, the necessary delay of the colour-formation is, as previously described, achieved with the help of a non-colour-forming substrate $S_O$ in the layer 60.

Numerous variations of the principles according to the present invention can be envisaged which differ from the preferred embodiments illustrated in FIGS. 1 to 3. In particular, each of these three embodiments is directed towards the determination of an antigen as analyte. If, in contradistinction thereto, an antibody from a sample is to be determined, then the test construction in each example is to be so varied in known manner that everywhere where previously an antibody was described, an antigen is used and vice versa. Otherwise, the course of the reactions are corresponding.

The following Examples are given for the purpose of illustrating the present invention:

EXAMPLE 1

Test strip for the detection of β-hCG in urine according to FIG. 1

1. Test layer 20

Fab-anti-hCG-galactosidase conjugate is prepared from sheep anti-hCG serum (immunisation: D. M. Weir, Handbook of Experimental Immunology, A 2.8; Fab cleavage: M. E. Davis, A. J. Barrett and R. M. Hernbry, J. of Immunological Methods, 21, 305/1978; conjugation: T. Kitagawa in Enzyme Immuno-Assay, editors: E. Ishikawa, T. Kawai and K. Miyai, pub. Igaku-Shoiu, Tokyo and New York, 1981) and dissolved in an amount of 5 U/ml. in 10 mM potassium phosphate buffer, 5 mM magnesium chloride, 25 mM sodium chloride, 2% saccharose, 0.5% bovine serum albumin and 0.1% sodium azide (pH 7.0) in water.

The solution is used to impregnate tea bag paper 212 (Schoeller & Hoesch, Gernsbach, Federal Republic of Germany), followed by drying for 30 minutes at ambient temperature.

2Test layer 16

2.1. Fixing of galactosidase on latex.

1 g. of latex (Serva Unisphere, 2 μm., Serva, Heidelberg, Federal Republic of Germany) with free carboxyl groups is washed with 50 ml. water. To the latex suspension in 10 ml. water are added 100 mg. 1-ethyl-3-(3-dimethylaminopropyl)-carbodiimide hydrochloride (Serva Feinbiochemica). After 1 hour, 200 mg. β-galactosidase (Boehringer Mannheim GmbH) are added thereto and incubation continued for a further 2 hours. Thereafter, repeated washing is carried out with glycine-containing (100 mM) buffer (PBS) and then stored as a suspension at 4° C. (maximum about 48 hours). The activity of the fixed galactosidase is determined by a colorimetric test.

2.2. Fixing of chlorophenol red galactoside 1 g. of latex is activated with carbodiimide analogously to 2.1. Thereafter, 10 ml. of 400 ml. 1,6-diaminohexane (Sigma Chemie, Heidelberg, Federal Republic of Germany), pH 7 (titrated with 1N hydrochloric acid) are added thereto and incubated for a further 2 hours, followed by repeated washing with water.

1 g. of the croteine C derivatised latex thus obtained in 10 ml. phosphate-buffered physiological sodium chloride solution (PBS) is mixed with 10 ml. of 25% glutardialdehyde and stirred at ambient temperature for 2 hours. Thereafter, it is filtered off with suction, washed and suspended in 10 ml. PBS. To this is added 0.5 g. 4''-aminochlorophenol red $\beta$-galactoside according to European Patent Specification No. 0,146,866, stirred for 6 hours, reduced for 30 minutes with 0.4 g. sodium cyanide-borohydride, filtered off with suction, washed and dried.

2.3. Fixing of $\beta$-hCG

500 IU $\beta$-hCG (Boehringer Mannheim GmbH) are fixed on to latex analogously to the $\beta$-galactosidase coupling.

2.4. Production of reagent layer 16

About 10 g. of film mass are produced from:
1 g. $\beta$-hCG latex
1 g. chlorphenol red galactoside latex
0.5 g. $\beta$-galactosidase latex (about 80 U)
1 g. vinyl propionate-vinyl acetate co-polymer (Propiofan 70 D, BASF, Federal Republic of Germany)
3.5 g. 1.4% alginate solution (Kelco, Bremen, Federal Republic of Germany)
40 mg. Tween 20 (Serva, Heidelberg, Federal Republic of Germany)
3 ml. pBS.

The mixture is applied in a 0.15 mm. thickness to a 0.2 mm. thick white-pigmented polycarbonate foil (Lonza Werke AG, Waldshut, Federal Republic of Germany) and dried for 30 minutes at 35° C.

3. Test layer 18

40 mM Nitrovinylgalactoside in PBS are used to impregnate tea bag paper 212 (Schoeller & Hoesch, Gernsbach, Federal Republic of Germany) and dried at ambient temperature for 30 minutes.

4. Construction of a test strip

As base foil 12, there is used a melt adhesive-coated polyvinyl chloride foil. On to the PVC foil there is fixed the test layer 16 (polycarbonate foil), thereupon the test layer 18 and uppermost the test layer 20 with the help of a nylon mesh (filament thickness 0.06 mm., 45% free hole surface). Melt adhesive is used for the fixing. The test layer format is 6×6 mm.

5. Determination of hCG in urine

The test strip is dipped for 1 second in the urine sample and, after 8 minutes, evaluated visually. Depending upon the hCG concentration, there thereby result the following colour gradations:

| hCG concentration in the urine mU/ml. | reaction colour after 8 minutes |
|---|---|
| 0 | yellow |
| 100 | yellow with light brownish shade |
| 400 | clearly recognisable red-violet |
| 1000 | strongly red-violet |

The limit of detection fulfils the requirement for a pregnancy determination which, with a sensitivity of 300 U/ml., can detect a pregnancy on the third day after omission of menses.

EXAMPLE 2

Quantitative reflection-photometrically evaluable test carrier for theophylline in whole blood according to FIG. 2

1. Test layer 44

Fab-anti-theophylline-$\beta$-galactosidase conjugate is produced by immunising sheep with theophylline-8-carboxypropyl-edestine. Fab cleavage and conjugation with $\beta$-galactosidase take place as in Example 1. The conjugate is used to impregnate paper in an amount of 100 U/ml. in the same buffer and in the same way as in Example 1.

2. Test layer 48

2.1. Fixing of theophylline 1 g. of latex is reacted analogously to 2.1 of Example 1 with 100 mg. theophylline-polyhapten (theophylline-8-carboxypropyl-IGG (8:1=theophylline: IGG) instead of $\beta$-galactosidase.

2.2. About 10 g. of film mass are prepared from:
1 g. theophylline latex
1 g. chlorophenol red galactoside latex (prepared as in Example 1)
10 mM nitrophenol galactoside
1 g. vinyl acetate-vinyl propionate co-polymer (Propiofan 70 D)
2.5 g. 1.4% alginate solution
40 mg. Tween 20
3 ml. PBS The mixture is applied in a thickness of 0.15 mm. to a 0.2 mm. thick clear polycarbonate foil one side of which is matt (Lonza), and dried for 30 minutes at 35° C.

3. Construction of the test carrier

The test carrier is constructed according to FIG. 2. The base foil 32 consists of 0.3 mm. thick polystyrene. A melt adhesive is used for fixing the layers.

4. Determination of theophylline in whole blood

30 $\mu$l. of whole blood are pipetted on to the glass fibre fleece 42 and the test carrier is evaluated with the reflection photometric analysis apparatus "Reflotron" (Boehringer Mannheim GmbH). The apparatus is so programmed that the flap 48 is pressed on after 2 minutes. Within this time, the plasma is separated off, the antibody-enzyme conjugate is dissolved and the binding reaction between the theophylline in the sample and the conjugate has taken place. Furthermore, the apparatus is so programmed that 7 minutes after the pressing on of the flap 48, the remission is measured. The following measurement value gradations are achieved:

| theophylline (mg./l.) | % remission |
|---|---|
| 0 | 63 |
| 1 | 62 |
| 3 | 58 |
| 10 | 42 |
| 30 | 21 |
| 45 | 18 |

It can be seen that the change of the theophylline concentration in the clinically relevant range leads to a strong change of remission, a high measurement exactitude thereby being achieved.

As will be understood by a person of ordinary skill in this art, the term "incubation" and "incubating" as used herein means reacting the components involved at an appropriate temperature which brings about the desired reaction. Typically, this temperature is room temperature, but may be a lower or higher temperature, depending on the particular components and reaction conditions involved.

We claim:

1. A process for the determination of an analyte in a sample, in which process there are used two biomaterial binding components which are specifically bindable with one another and one of which is specifically bindable with said analyte, one of said binding components BfE being enzyme-labelled with a labelling enzyme E and not carrier-fixed and the other binding component Bb being carrier-fixed, said process comprising the steps of:
   incubating said analyte with at least one of said binding components;
   incubating said binding components with one another so that a specific binding reaction takes place between them, wherein during said specific binding reaction said incubating is carried out in the presence of a non-fixed substrate $S_O$ of E which does not produce a detection signal upon undergoing an enzyme-catalyzed reaction with E and in the presence of a carrier-fixed substrate S of E which does produce a detection signal upon undergoing an enzyme catalyzed reaction with E, the amount or presence of BfE not bound to Bb after said specific binding reaction being a measure of the concentration or presence of said analyte in said sample; and
   determining said amount or presence of unbound BfE by allowing the labelling enzyme to undergo an enzyme catalyzed reaction with S;
   wherein $S_O$ is chosen with regard to the amount used and affinity to E in relation to the amount of S and its affinity to E and in relation to the total activity of E that, upon simultaneous incubation of said unbound BfE with $S_O$ and S, the enzyme-catalyzed reaction of S is delayed until the specific binding reaction between said binding components is substantially complete.

2. A process according to claim 1, wherein said analyte is a body fluid.

3. A process according to claim 2, wherein said carrier-fixed binding component is a biomaterial which is specifically bindable not only with said analyte, but also with said enzyme-labelled, non-carrier-fixed binding component.

4. A process according to claim 2, wherein said non-carrier-fixed, enzyme-labelled binding component is a biomaterial which is specifically bindable not only with said analyte, but also with said carrier-fixed binding component.

5. A process according to claim 4, wherein said enzyme-labelled, non-carrier-fixed binding component is incubated with said analyte prior to said incubation step between said enzyme-labelled, non-carrier-fixed binding component and said carrier-fixed binding component.

6. A process according to claim 4, wherein said analyte is incubated simultaneously with the incubation of said enzyme-labelled, non-carrier-fixed binding component with said carrier-fixed binding component.

7. A process according to claim 2, wherein said enzyme-labelled, non-carrier-fixed binding component is an enzyme-labelled antigen and said carrier-fixed binding component is a carrier-fixed antibody for said antigen.

8. A process according to claim 2, wherein said enzyme-labelled, non-carrier-fixed binding component is an enzyme-labelled antibody and said carrier-fixed binding component is a carrier-fixed antigen which is specific for said antibody.

9. A process according to claim 2, wherein incubation is additionally carried out with said labelling enzyme in a carrier-fixed form.

10. A process according to claim 2, wherein incubation is additionally carried out with said non-carrier-fixed binding component without enzyme labelling.

11. A process according to claim 2, wherein said labelling enzyme has a higher affinity towards said non-fixed substrate which does not produce a detection signal than towards said carrier-fixed substrate producing a detection signal.

12. A test carrier for the determination of an analyte in a sample, said test carrier comprising:
   1) a reaction zone means for receiving a sample of said analyte and for simultaneously incubating said analyte; and
   2) the following reaction components:
      a) a soluble binding component BfE which is enzyme-labelled with a labelling enzyme E;
      b) a carrier fixed binding component Bb which is specifically bindable with the soluble BfE, one of said binding components being specifically bindable with the analyte;
      c) a free substrate $S_O$ for E which, upon undergoing an enzyme-catalyzed reaction with the labelling enzyme, does not produce a detection signal; and
      d) a carrier-fixed substrate S for E which, upon undergoing a reaction catalyzed by E, produces a detection signal, said E, said $S_O$, and said S being provided and selected in an amount such that upon the simultaneous incubation the enzyme-catalyzed reaction of S is delayed until the specific binding reactions between BfE and Bb are substantially complete.

13. A test carrier according to claim 13, wherein said reaction zone contains said labelling enzyme in carrier-fixed form and in such an arrangement that it is also simultaneously incubated.

14. A test carrier according to claim 13, wherein said reaction zone contains a non-carrier-fixed binding component without enzyme labelling in such an arrangement that it is also simultaneously incubated.

15. A test carrier according to claim 13, wherein said reaction zone includes several layers containing said reaction components which are so arranged that a liquid exchange occurs during at least a part of the time of the test.

16. A test carrier according to claim 15, wherein a carrier-fixed, enzyme-labelled binding component is contained in a layer which does not simultaneously contain at least one of said substrates.

17. A test carrier according to claim 15, wherein an enzyme-labelled, non-carrier-fixed binding component and said carrier-fixed binding components are contained in separate layers.

18. A test carrier for the determination of an analyte in a sample, said test carrier comprising:

reaction zone means for receiving a sample of said analyte and incubating said analyte with an excess of a soluble binding component which is specifically bindable with said analyte and which is enzyme-labelled with a labelling enzyme to form an analyte conjugate;

a flap moveable into contact with said reaction zone means, said flap comprising the following reaction components:

a carrier-fixed binding component which is specifically bindable with the soluble binding components;

a free substrate for said labelling enzyme which, upon undergoing an enzyme-catalyzed reaction with the labelling enzyme, does not produce a detection signal; and a carrier fixed substrate for said labelling enzyme which, upon undergoing an enzyme-catalyzed reaction with the labelling enzyme, does produce a detection signal;

said labelling enzyme, said free substrate and said carrier-fixed substrate cooperating with respect to their nature and amounts such that, upon incubation of said binding components in said flap with an excess soluble binding component and said analyte conjugate, the enzyme catalyzed reaction of the carrier-fixed substrate to produce a detection signal is delayed until the specific binding reactions between excess enzyme labelled binding component and the carrier-fixed binding component are substantially complete.

19. A process for the determination of an analyte in a sample, said process comprising:

incubating:

a) said analyte;

b) two biomaterial binding components which are capable of undergoing a specific binding reaction to specifically bind with one another, and one of which is specifically bindable with the analyte, one of the binding components being free BfE and enzyme labelled with a labelling enzyme E, and the other binding component being carrier-fixed Bb;

c) a free substrate $S_O$ of E which does not produce a detection signal upon undergoing an enzyme-catalyzed reaction with E;

d) a carrier-fixed substrate S of E which does produce a detection signal upon undergoing an enzyme-catalyzed reaction with E; and determining the amount or presence of BfE not bound to Bb after completion of the incubation step to measure the concentration or presence of the analyte in the sample by allowing E to cause an enzyme catalyzed reaction of S, but delaying the enzyme-catalyzed reaction of S until the specific binding reaction between the binding components is substantially complete.

* * * * *